US00PP34170P3

(12) United States Plant Patent
Post

(10) Patent No.: US PP34,170 P3
(45) Date of Patent: Apr. 26, 2022

(54) ***CHRYSANTHEMUM* PLANT NAMED 'DLFSTAR1'**

(50) Latin Name: ***Chrysanthemum* X *morifolium***
Varietal Denomination: DLFSTAR1

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/395,285

(22) Filed: Aug. 5, 2021

(65) Prior Publication Data

US 2022/0046841 P1 Feb. 10, 2022

Related U.S. Application Data

(60) Provisional application No. 63/062,375, filed on Aug. 6, 2020.

(51) Int. Cl.
*A01H 5/02* (2018.01)
*A01H 6/14* (2018.01)

(52) U.S. Cl.
USPC ..... Plt./294

(58) Field of Classification Search
USPC ..... Plt./263.1, 284, 286, 294
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Chrysanthemum* plant named 'DLFSTAR1', characterized by its upright plant habit; vigorous growth habit; dark green-colored leaves; uniform flowering habit; strong upright flowering stems; large incurved spider-type inflorescences with white-colored ray florets; resistance to Fusarium; relative tolerance to low and high production temperatures; and good postproduction longevity.

2 Drawing Sheets

Figure 1:
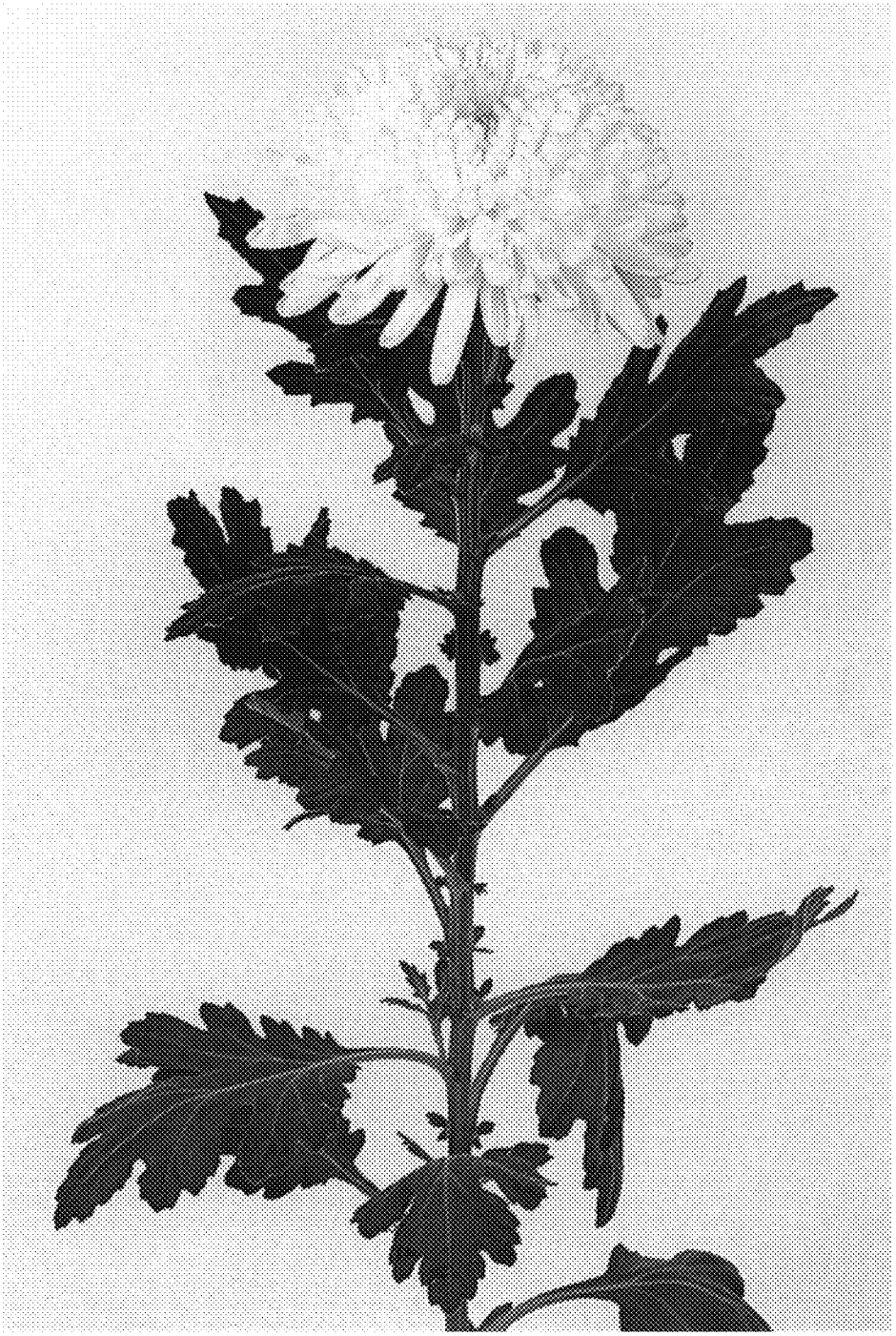

Botanical designation: *Chrysanthemum* X *morifolium*.
Cultivar denomination: 'DLFSTAR1'.

CROSS-REFERENCED TO CLOSELY-RELATED APPLICATIONS

Title: Varieties of *Chrysanthemum* Plants
Inventor/Applicant: Arie Gerard Post
Filed: Aug. 6, 2020
Ser. No.: 63/062,375
Inventor/Applicant hereby claims the benefit of this provisional U.S. Patent Application.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Jul. 16, 2020, application number A202696. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFSTAR1'.

The new *Chrysanthemum* plant is a product of a planned breeding program conducted by the Inventor in Maasdijk, The Netherlands. The objective of the breeding program is to create new cut flower *Chrysanthemum* plants with attractive inflorescences.

The new *Chrysanthemum* plant originated from a cross-pollination in March, 2012 of a proprietary selection of *Chrysanthemum* x *morifolium* identified as code number db 11359, not patented, as the female, or seed, parent with a proprietary selection of *Chrysanthemum* x *morifolium* identified as code number db 42520, not patented, as the male, or pollen, parent. The new *Chrysanthemum* plant was discovered and selected as a single flowering plant from within the progeny of the stated cross-pollination in a controlled greenhouse environment in Maasdijk, The Netherlands in October, 2014.

Asexual reproduction of the new *Chrysanthemum* plant by vegetative terminal cuttings since October, 2014 in a controlled greenhouse environment in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFSTAR1'. These characteristics in combination distinguish 'DLFSTAR1' as a new and distinct *Chrysanthemum* plant:

1. Upright plant habit; vigorous growth habit.
2. Dark green-colored leaves.
3. Uniform flowering habit.
4. Strong upright flowering stems.
5. Large incurved spider-type inflorescences with white-colored ray florets.
6. Resistant to Fusarium (*Fusarium oxysporum*).
7. Relatively tolerant to low and high production temperatures.
8. Good postproduction longevity.

Plants of the new *Chrysanthemum* differ primarily from plants of the female parent selection in ray floret shape as ray florets of plants of the new *Chrysanthemum* are incurved tubular whereas ray florets of plants of the female parent selection are spatulate.

Plants of the new *Chrysanthemum* differ primarily from plants of the male parent selection in ray floret shape as ray florets of plants of the new *Chrysanthemum* are incurved tubular whereas ray florets of plants of the male parent selection are ligulate. In addition, inflorescences of plants of the new *Chrysanthemum* are incurved types whereas inflorescences of plants of the male parent selection are semi-double types.

Plants of the new *Chrysanthemum* can be compared to plants of *Chrysanthemum* X *morifolium* 'DLFFALC1', not patented. In side-by-side comparisons, plants of the new *Chrysanthemum* differ primarily from plants of 'DLFFALC1' in ray floret shape as ray florets of plants of the new *Chrysanthemum* have emarginate apices whereas ray florets of plants of 'DLFFALC1' have praemorse apices.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) comprises a side perspective view of a typical flowering stem of 'DLFSTAR1' grown as a disbud-type cut flower.

Figure 2:
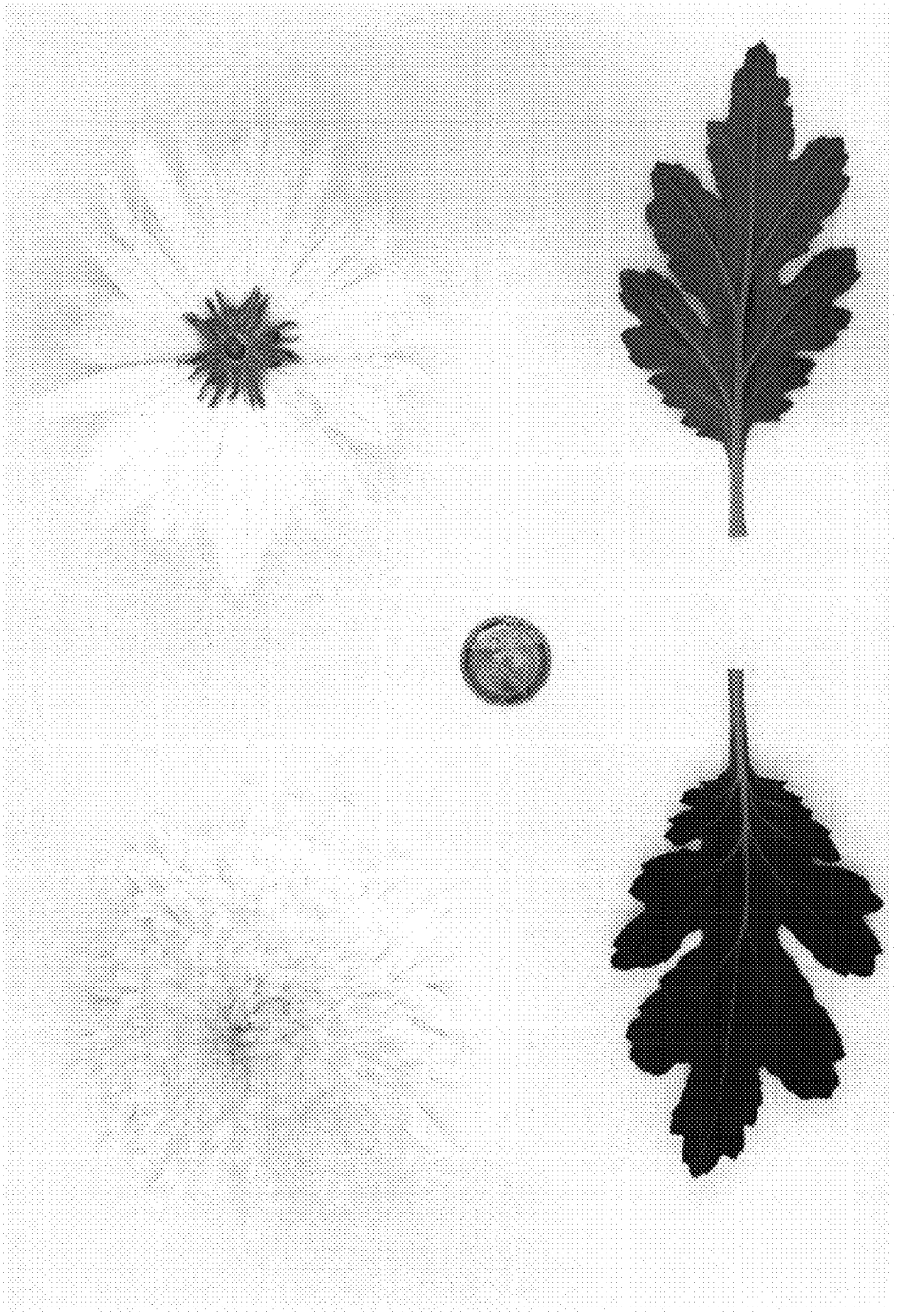

The photograph on the second sheet (FIG. 2) is a close-up view of upper (left) and lower (right) surfaces of typical leaves (bottom of photographic sheet) and inflorescences (top of photographic sheet).

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem disbud-type plants (unless otherwise noted) and were ten weeks old when the photographs were taken and eleven weeks old when the description was taken. In the following description, color references are made to The Royal Horticultural Society Colour Chart, 2015 Edition, except where general terms of ordinary dictionary significance are used.

Botanical classification: *Chrysanthemum* X *morifolium* 'DLFSTAR1'.

Parentage:

*Female, or seed, parent*.—Proprietary selection of *Chrysanthemum* x *morifolium* identified as code number db 11359, not patented.

*Male, or pollen, parent*.—Proprietary selection of *Chrysanthemum* x *morifolium* identified as code number db 42520, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous incurved spider-type cut flower that is typically grown as a single stem disbud-type; upright plant habit; vigorous growth habit and rapid growth rate.

*Plant height, soil level to top of foliar plane*.—About 61.6 cm.

*Plant height, soil level to top of inflorescence plane*.—About 64.6 cm.

*Plant (spray) diameter*.—About 21.8 cm.

*Flowering stem length*.—About 55 cm.

*Flowering stem diameter*.—About 7 mm.

*Flowering stem internode length*.—About 2.8 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 143C.

*Flowering stem color, developed*.—Close to 137B and 146B.

*Leaf description*.—Arrangement: Alternate; simple. Length: About 14.5 cm. Width: About 9 cm. Shape, in overall outline: Ovate. Apex: Abruptly acute, minute. Base: Attenuate. Margin: Palmately lobed, coarsely crenate to dentate; sinuses convergent and medium in depth to deep. Texture and luster, upper surface: Moderately to densely pubescent, not rugose; moderately velvety; slightly glossy. Texture and luster, lower surface: Moderately to densely pubescent, prominent venation; slightly velvety; matte to slightly glossy. Venation pattern: Pinnate, reticulate. Color: Developing leaves, upper surface: Close to 137A to 137B. Developing leaves, lower surface: Close to between 138B and 147B. Fully developed leaves, upper surface: Close to between NN137A and 147A; venation, close to 147B. Fully developed leaves, lower surface: Close to 147B; venation, close to 146B. Petioles: Length: About 2.6 cm. Diameter: About 3.5 mm by 4 mm. Strength: Moderately strong. Texture and luster, upper surface: Densely pubescent; glossy. Texture and luster, lower surface: Densely pubescent; moderately glossy. Color, upper surface: Close to 146B; edges, close to 137A. Color, lower surface: Close to 146B; edges, close to 147B. Stipules: Quantity and appearance: Two leafy stipules, opposite, at the petiole attachment to the stem. Length: About 9 mm. Width: About 1.2 cm. Shape, in overall outline: Broadly obovate to reniform; occasionally cleft with one to three medium in depth incisions distally. Texture and luster, upper surface: Moderately to densely pubescent; slightly glossy. Texture and luster, lower surface: Moderately to densely pubescent; matte to slightly glossy. Color, upper surface: Close to between NN137A and 147A. Color, lower surface: Close to 147B.

Inflorescence description:

*Appearance*.—Incurved spider-type inflorescence form with tubular-shaped ray florets and tubular disc florets; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 56 days later when grown as a disbud-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a disbud-type, only the terminal inflorescence is allowed to developed; if grown as a spray-type, about eleven inflorescences develop per flowering stem.

*Inflorescence size*.—Diameter, grown as a disbud-type: About 13.9 cm. Depth (height), grown as a disbud-type: About 4.4 cm. Disc diameter, grown as a disbud-type: About 1.3 cm. Diameter, grown as a spray-type: About 8.8 cm. Depth (height), grown as a spray-type: About 3.9 cm. Disc diameter, grown as a spray-type: About 4 mm.

*Receptacles*.—Height, grown as a disbud-type: About 8 mm. Diameter, grown as a disbud-type: About 1.4 cm. Height, grown as a spray-type: About 4 mm. Diameter, grown as a spray-type: About 7 mm. Shape: Flattened globular. Color: Close to 146A and 146B.

*Inflorescence buds*.—Height: About 1.8 cm. Diameter: About 2.3 cm. Shape: Flattened globular. Texture and luster: Distally, smooth and glabrous; proximally, moderately pubescent; slightly glossy. Color: Developing involucral bracts, close to NN137B and NN137C; developing ray florets, close to 150C.

*Ray florets*.—Quantity and arrangement: About 320 arranged in about twelve whorls. Length, when grown as a disbud-type: About 5 cm; varying from about 1.1 cm to 7 cm. Width, when grown as a disbud-type: About 1 cm; varying from 0.2 mm to 1.4 cm. Length, when grown as a spray-type: About 3.4 cm; varying from about 1.1 cm to 4.7 cm. Width, when grown as a spray-type: About 1 cm; varying from 0.2 cm to 1.4 cm. Shape: Tubular. Apex: Emarginate. Base: Fused. Margin, free-part: Entire; not undulate. Aspect: About 20° to 80° from vertical. Texture and luster, upper surface: Smooth, glabrous; slightly velvety; matte. Texture and luster, lower surface: Smooth, glabrous; slightly velvety; slightly glossy. Color: When opening, upper and lower surfaces: Close to 155C; towards the apex, close to 145C. Fully opened, upper surface: Close to NN155D; towards the base, close to 145B to 145C; venation, similar to lamina colors; color does not change with subsequent development. Fully opened, lower surface: Close to NN155D; towards the base, close to 145B to 145C; venation, close to NN155C to NN155D; color does not change with subsequent development.

*Disc florets*.—Quantity and arrangement: About 100, randomly positioned at the center of the receptacle. Length: About 5.5 mm. Diameter: About 1 mm. Shape: Lower 85% fused into a tube; upper 15% free. Apex: Narrowly acute. Margin, free-part: Entire. Texture and luster, inner and outer surfaces: Smooth, glabrous; glossy. Color, when opening, inner and outer surfaces: Close to 151D; distally, close to 144B. Color, fully opened, inner and outer surfaces: Close to 151D; distally, close to 144B.

*Involucral bracts*.—Quantity and arrangement: About 26 arranged in about two whorls. Length: About 1.4 cm. Width: About 4 mm. Shape: Narrowly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to 146B; lateral margins, translucent and close to 157B and 157C and apical margins tinged with close to 199B to 199C; midvein, close to 147A. Color, lower surface: Close to between 137A and 143A; lateral margins, translucent and close to 157B and 157C and apical margins tinged with close to 199B to 199C.

*Peduncles*.—Length, terminal peduncle: About 4.9 cm. Diameter, terminal peduncle: About 7 mm. Length, third peduncle, grown as a spray-type: About 7.3 cm. Diameter, third peduncle, grown as a spray-type: About 4 mm. Strength: Strong. Aspect, terminal peduncle: Upright. Aspect, third peduncle, grown as a spray-type: About 45° from the flowering stem axis. Texture and luster: Densely pubescent; slightly glossy. Color: Close to between 137C and 138A to 138B.

*Reproductive organs*.—Androecium: Present on disc florets only. Quantity: About three per floret, deformed. Filament length: About 2.5 mm. Filament color: Close to 151C. Anthers: Anther development has not been observed. Gynoecium: Present on both ray and disc florets. Quantity: One per floret. Pistil length: About 6 mm. Style length: About 5 mm. Style color: Close to 151C. Stigma diameter: About 1 mm. Stigma shape: Cleft to three-parted, decurrent. Stigma color: Close to 151B. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to Fusarium Wilt (*Fusarium oxysporum* spp. *chrysanthemi* (strain FoNL1)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFSTAR1' as illustrated and described.

* * * * *